United States Patent
Fish et al.

(10) Patent No.: US 10,119,129 B2
(45) Date of Patent: Nov. 6, 2018

(54) **ENZYME COMPLEX FROM *TRICHODERMA REESEI* AND *P. FUNICULOSUM* ENZYMES**

(75) Inventors: Neville Marshall Fish, Stockport (GB); Lone Brønd Miller, Viby J (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 829 days.

(21) Appl. No.: 13/318,850

(22) PCT Filed: May 7, 2010

(86) PCT No.: PCT/EP2010/056259
§ 371 (c)(1),
(2), (4) Date: Nov. 4, 2011

(87) PCT Pub. No.: WO2010/128140
PCT Pub. Date: Nov. 11, 2010

(65) Prior Publication Data
US 2012/0058510 A1    Mar. 8, 2012
US 2012/0270263 A9    Oct. 25, 2012

Related U.S. Application Data

(60) Provisional application No. 61/176,162, filed on May 7, 2009.

(30) Foreign Application Priority Data

May 7, 2009    (EP) .................... 09159680

(51) Int. Cl.
| | | |
|---|---|---|
| *C12P 1/00* | (2006.01) | |
| *C12N 9/42* | (2006.01) | |
| *A23L 2/02* | (2006.01) | |
| *C12C 5/00* | (2006.01) | |
| *C12C 7/04* | (2006.01) | |
| *C12G 3/12* | (2006.01) | |
| *C12N 1/14* | (2006.01) | |
| *C12P 7/06* | (2006.01) | |
| *C12R 1/80* | (2006.01) | |
| *C12R 1/885* | (2006.01) | |
| *C12N 9/24* | (2006.01) | |

(52) U.S. Cl.
CPC .............. *C12N 9/2437* (2013.01); *A23L 2/02* (2013.01); *C12C 5/004* (2013.01); *C12C 5/006* (2013.01); *C12C 7/04* (2013.01); *C12G 3/12* (2013.01); *C12N 1/14* (2013.01); *C12N 9/244* (2013.01); *C12N 9/2482* (2013.01); *C12P 7/06* (2013.01); *C12R 1/80* (2013.01); *C12R 1/885* (2013.01); *C12Y 302/01004* (2013.01); *C12Y 302/01006* (2013.01); *C12Y 302/01008* (2013.01); *Y02E 50/17* (2013.01)

(58) Field of Classification Search
None
See application file for complete search history.

(56) References Cited

U.S. PATENT DOCUMENTS 6,541,233 B1    4/2003   Hillen et al.
2003/0108642 A1*  6/2003   Sabatier et al. ................ 426/37

FOREIGN PATENT DOCUMENTS

| WO | WO 97/42301 A1 | 11/1997 |
|---|---|---|
| WO | WO 99/57325 A2 | 11/1999 |
| WO | WO 2004/087889 A1 | 10/2004 |
| WO | WO 2005/059084 A1 | 6/2005 |
| WO | WO 2005/118769 A1 | 12/2005 |
| WO | WO 2008/023060 A1 | 2/2008 |

OTHER PUBLICATIONS

Biely et al. "The endo-I,4-P-glucanase I from *Trichoderma reesei*" Eur. J. Biochem. 200, 157-163 (1991).*
Brenda "Information on EC 3.2.1.4—cellulase" Accessed Oct. 16, 2014 at http://www.brenda-enzymes.org/, 1 pg.*
Fao "Mixed Xylanase, β-Glucanase Enzyme Preparation, produced by a strain of Humicola Insolens" obtained from Food and Agriculture Organization of the United Nations at http://www.fao.org/ag/agn/jecfa-additives/specs/Monograph1/Additive-286.pdf, 2003, 6 pgs.*
Mishra et al. "Hydrolysis of Lignocelluloses by *Penicillium funiculosum* Cellulase" Biotechnology and Bioengineering, vol. XXVI, pp. 370-373 (1984).*
Rao et al. "Effect of Pretreatment on the Hydrolysis of Cellulose by *Penicillium funiculosum* Cellulase and Recovery of Enzyme" Biotechnology and Bioengineering, vol. XXV, pp. 1863-1871 (1983).*
JPH van Wyk "Sacchari®cation of paper products by cellulase from *Penicillium funiculosum* and Trichoderma reesei" Biomass and Bioenergy 16 (1999) 239-242.*
Withers "Glycoside Hydrolase Family 11" in CAZypedia, available at URL http://www.cazypedia.org/, accessed Apr. 8, 2015.*
Danisco, "Danisco's food & beverage enzye team to launch Laminex® Super 3G, a new brewing enzyme," Press Release, 2009, 3 pages.

* cited by examiner

*Primary Examiner* — Thane Underdahl

(57) ABSTRACT

The invention relates to an improved enzyme complex having a plurality of enzyme activities of an expression product obtained by fermentation of the genus *Trichoderma* in combination with one or more enzymes of a different fungus strain.

14 Claims, 3 Drawing Sheets

ENZYME COMPLEX FROM *TRICHODERMA REESEI* AND *P. FUNICULOSUM* ENZYMES

CROSS-REFERENCE TO RELATED APPLICATIONS

Figure 1:
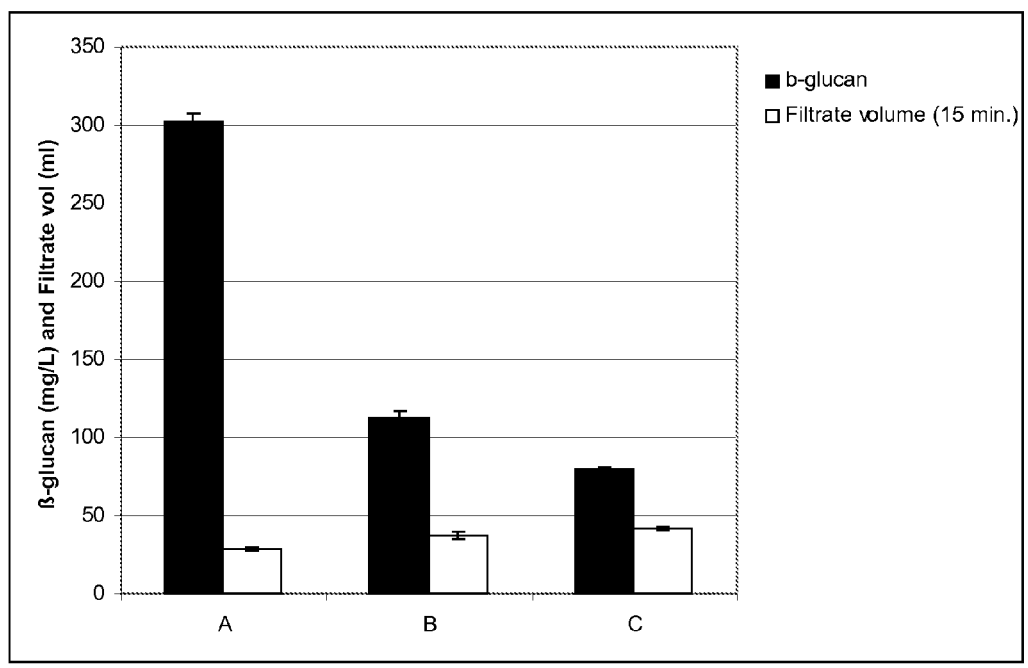

This application is the U.S. National Stage of International Application PCT/EP2010/056259 filed May 7, 2010, which designates the U.S. and was published by the International Bureau in English on Nov. 11, 2010, and which claims the benefit of European Patent Application No. 09159680.9, filed May 7, 2009, and U.S. Provisional Application No. 61/176,162, filed May 7, 2009, all of which are hereby incorporated herein in their entirety by reference.

FIELD OF THE INVENTION

The invention relates to an improved enzyme complex having a plurality of enzyme activities of an expression product obtained by fermentation of the genus *Trichoderma* in combination with one or more enzymes of a different species of a fungus strain.

BACKGROUND OF THE INVENTION

The use of enzymes in beer production is well known. Application of enzymes to the mashing step to improve mash filterability and increase extract yield is described in WO 97/42302.

WO2005118769 and WO2005059084 relates to a mashing and filtration step in a process for the production of beer, and to enzymatic compositions for use in such a process.

WO1999057325 relates to strains of *Penicillium funiculosum,* to new enzyme mixtures obtained from it and nucleic sequences thereto.

However, there is a need for improved enzyme complexes useful in the productions of food products, such as in the mashing, cooking and filtration steps in the production of an alcoholic beverage, such as beer or whiskey.

OBJECT OF THE INVENTION

It is an object of embodiments of the invention to provide an improved enzyme complex enabling improved productions methods in the preparation of e.g. food products, such as in the mashing, cooking and/or filtration steps in the production of an alcoholic beverage, such as beer or whiskey, or a biofuel.

SUMMARY OF THE INVENTION

It has been found by the present inventor(s) that by combining an expression product obtained by fermentation of a species of the genus *Trichoderma* and specific enzymes of any one different species of a fungus, improved properties of the enzyme complex are obtained.

So, in a first aspect the present invention relates to an enzyme complex derived from a combination of:
 a. An expression product obtained by fermentation of a species of the genus *Trichoderma;* and
 b. One or more enzymes of any one different species of the kingdom fungi selected from a xylanase (EC 3.2.1.8), a cellulase (EC 3.2.1.4), and a beta-glucanase (EC 3.2.1.6);
and wherein at least about 61% of the beta-1,4-endoglucan hydrolase activity as measured by the "Assay 1" method as described herein is derived from fermentation of the genus *Trichoderma*.

It is to be understood that "any one different species of the kingdom fungi" refers to a species different from the species of the genus *Trichoderma* in (a).

In a second aspect, the present invention relates to an enzyme complex derived from a combination of:
 a. At least about 61% of an expression product obtained by fermentation of the genus *Trichoderma;* and
 b. Less than about 39% of an expression product obtained by fermentation of a different fungus of the genus *Penicillium;*
wherein the percentages are based on the beta-1,4-endoglucan hydrolase activity as measured by the "Assay 1" method as described herein.

In a third aspect the present invention relates to a process for the production of an enzyme complex, the process comprising the steps of
 a. fermentation of the genus *Trichoderma* in a medium to obtain a fermentation broth;
 b. fermentation of the genus *Penicillium* in a medium to obtain a fermentation broth, and
 c. recovery and combination of each enzyme complex derived from step a) and b) in the form of a cell free broth from said fermentations to obtain an enzyme complex, wherein at least about 61% of the beta-1,4-endoglucan hydrolase activity as measured by the "Assay 1" method as described herein is derived from fermentation of the genus *Trichoderma*.

In a further aspect the present invention relates to the use of an enzyme complex according to the invention, in a process for production of a brewing mash, such as in the production of a malt beverage, such as a beer, such as a malt beverage beer, and/or in a whiskey production and/or in the biofuel production.

In a further aspect the present invention relates to the use of an enzyme complex according to the invention, in the production of fruit juice, wine, grain processing, fuel alcohol, and potable alcohol.

In a further aspect the present invention relates to an enzyme complex derived from a combination of:
 a. An expression product obtained by fermentation of a species of the genus *Trichoderma;* and
 b. One or more enzymes of any one different species of the kingdom fungi selected from a family 11 xylanase (EC 3.2.1.8), a cellulase (EC 3.2.1.4), and a beta-glucanase (EC 3.2.1.6);
and wherein at least about 61% of the beta-1,4-endoglucan hydrolase activity as measured by the "Assay 1" method as described herein is derived from fermentation of the genus *Trichoderma*.

LEGENDS TO THE FIGURE

FIG. 1. Lab scale mash trial 1—wort β-glucan and filtration volume.

Figure 2:
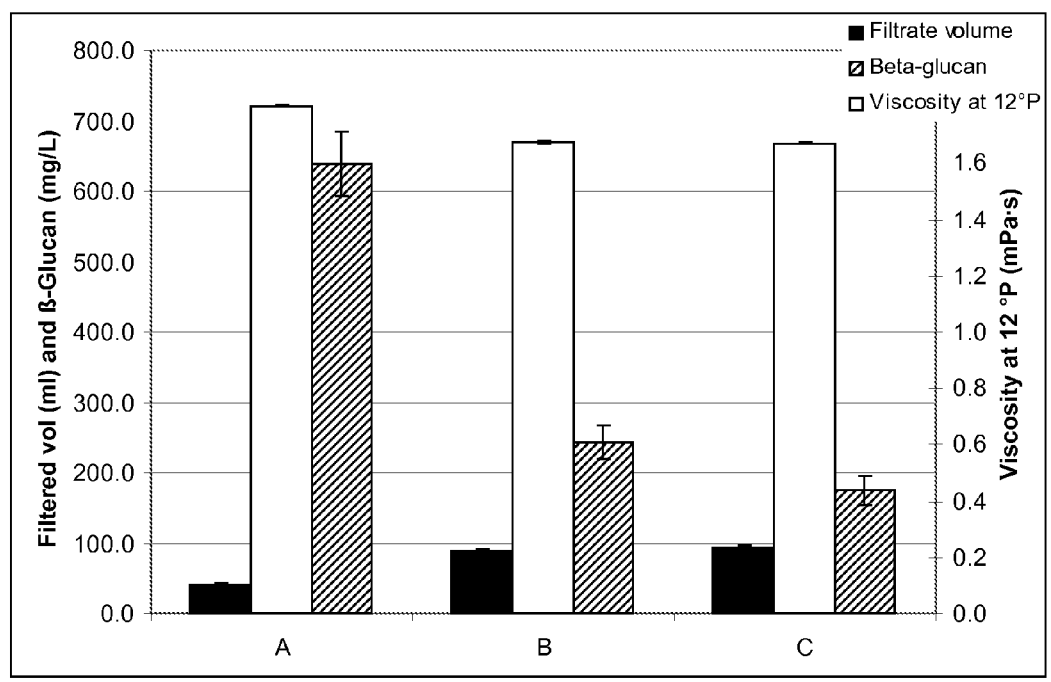

FIG. 2. Lab scale mash trail 2—wort filtration volumes, residual β-Glucan and viscosity (at 12° P) data.

Figure 3:
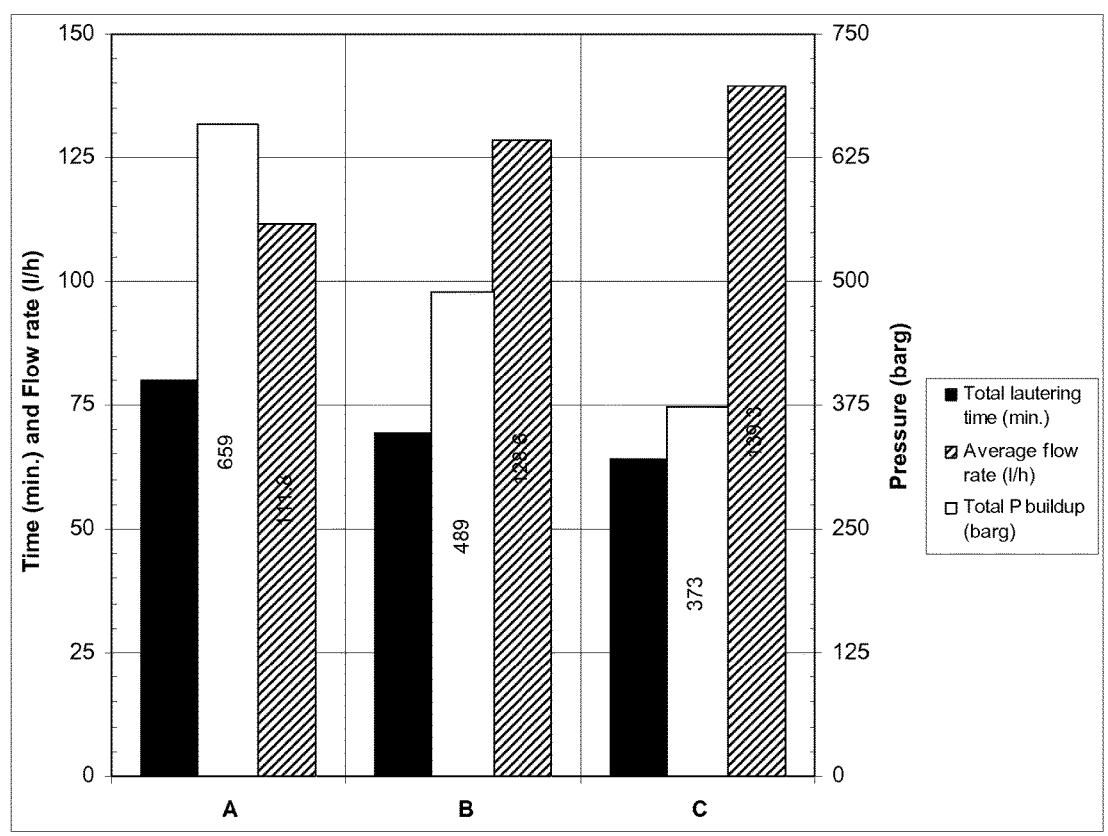

FIG. 3. Pilot trial lautering data—Total lautering time, Average flow rate and total pressure build up. A: Negative control, No enzyme control; B: LAMINEX® Super at 0.20 kg/ton; C: The LAMINEX® XG (LAMINEX® Super 1.5+ 50% more *T. reesei* activity) at 0.133 kg/ton.

DETAILED DISCLOSURE OF THE INVENTION

Beer is traditionally referred to as an alcoholic beverage derived from malt, such as malt derived from barley, and optionally adjuncts, such as cereal grains, and flavoured with hops. Included within the term "beer" is any fermented wort, produced by the brewing and fermentation of a starch-containing material, mainly derived from cereal grains, such as malted barley. Wheat, maize, and rice may also be used.

As used herein, the term "malt beverage" includes such foam forming fermented malt beverages as full malted beer, ale, dry beer, near beer, light beer, low alcohol beer, low calorie beer, porter, bock beer, stout, malt liquor, non-alcoholic malt liquor and the like. The term "malt beverages" also includes non-foaming beer and alternative malt beverages such as fruit flavoured malt beverages, e. g., citrus flavoured, such as lemon-, orange-, lime-, or berry-flavoured malt beverages, liquor flavoured malt beverages, e. g., vodka-, rum-, or tequila-flavoured malt liquor, or coffee flavoured malt beverages, such as caffeine-flavoured malt liquor, and the like.

Beer can be made from a variety of grains by essentially the same process. All grain starches are glucose homopolymers in which the glucose residues are linked by either alpha-1,4- or alpha-1,6-bonds, with the former predominating.

The process of making fermented malt beverages is commonly referred to as brewing. The principal raw materials used in making these beverages are water, hops and malt. In addition, adjuncts such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, and syrups, such as corn syrup, sugar cane syrup, inverted sugar syrup, barley and/or wheat syrups, and the like may be used as a source of starch. The starch will eventually be converted into dextrins and fermentable sugars.

For a number of reasons, the malt, which is produced principally from selected varieties of barley, has the greatest effect on the overall character and quality of the beer. First, the malt is the primary flavouring agent in beer. Second, the malt provides the major portion of the fermentable sugar. Third, the malt provides the proteins, which will contribute to the body and foam character of the beer. Fourth, the malt provides the necessary enzymatic activity during mashing.

Hops also contribute significantly to beer quality, including flavouring. In particular, hops (or hops constituents) add desirable bittering substances to the beer. In addition, the hops act as protein precipitants, establish preservative agents and aid in foam formation and stabilization.

The process for making beer is well known in the art, but briefly, it involves five steps: (a) mashing and/or adjunct cooking (b) wort separation and extraction (c) boiling and hopping of wort (d) cooling, fermentation and storage, and (e) maturation, processing and packaging.

Typically, in the first step, milled or crushed malt is mixed with water and held for a period of time under controlled temperatures to permit the enzymes present in the malt to convert the starch present in the malt into fermentable sugars.

In the second step, the mash is transferred to a "lauter tun" or mash filter where the liquid is separated from the grain residue. This sweet liquid is called "wort" and the left over grain residue is called "spent grain". The mash is typically subjected to an extraction, which involves adding water to the mash in order to recover the residual soluble extract from the spent grain.

In the third step, the wort is boiled vigorously. This sterilizes the wort and helps to develop the colour, flavour and odour. Hops are added at some point during the boiling.

In the fourth step, the wort is cooled and transferred to a fermentor, which either contains the yeast or to which yeast is added. The yeast converts the sugars by fermentation into alcohol and carbon dioxide gas; at the end of fermentation the fermentor is chilled or the fermentor may be chilled to stop fermentation. The yeast flocculates and is removed.

In the last step, the beer is cooled and stored for a period of time, during which the beer clarifies and its flavour develops, and any material that might impair the appearance, flavour and shelf life of the beer settles out. Prior to packaging, the beer is carbonated and, optionally, filtered and pasteurized.

After fermentation, a beverage is obtained which usually contains from about 2% to about 10% alcohol by weight. The non-fermentable carbohydrates are not converted during fermentation and form the majority of the dissolved solids in the final beer.

This residue remains because of the inability of malt amylases to hydrolyze the alpha-1,6-linkages of the starch. The non-fermentable carbohydrates contribute about 50 calories per 12 ounces of beer.

Recently, there has been a widespread popularization of brewed beverages called light beers, reduced calorie beers or low calorie beers, particularly in the U.S. market. As defined in the U.S., these beers have approximately 30% fewer calories than a manufacturer's "normal" beer.

Further information on conventional brewing processes, as well as definitions for terms used in the field of brewing technology to be applied for the present invention, may be found in "Technology Brewing and Malting" by Wolfgang Kunze of the Research and Teaching Institute of Brewing, Berlin (VLB), 2nd revised Edition 1999, ISBN 3-921690-39-0 or 3rd edition (2004): ISBN 3-921690-49-8.

Definitions

The term "enzyme complex" as used herein means in the present context a substantially cell-free composition comprising several enzymes having different enzymatic activity and/or classified under different Enzyme Commission numbers (EC number). When the "enzyme complex" is obtained by fermentation, it is the substantially cell-free fermentation broth, optionally the concentrated fermentation broth, which is included in the final product. It is to be understood that the term "enzyme complex" also encompasses a composition comprising several enzymes derived by two or more separate fermentation processes which may also involve different microorganisms. In some embodiments the enzyme complex is a food grade enzyme complex, which means that it may be used for the preparation of food products.

In some aspects of the invention, the enzyme complex according to the invention contains the side-activities necessary to degrade the very complex compounds of e.g. a mash in a brewing process. The term "side-activity" refers in the present context to the activities of an enzyme towards other substrates which is not its main substrate or it refers to other activities an enzyme complex may have other than its main activity.

In one aspect of the invention, the enzyme complex according to the invention comprises at least 5 different side-activities.

In one aspect of the invention, the enzyme complex according to the invention comprises at least 10 different side-activities.

In one aspect of the invention, the enzyme complex according to the invention comprises at least 15 different side-activities.

In one aspect of the invention, the enzyme complex according to the invention comprises at least 20 different side-activities.

Xylanases are classified in EC 3.2.1.8, EC 3.2.1.32, EC 3.2.1.136 and EC 3.2.1.156; activity may be measured e.g. as described in "Assay 2".

Endo-1,4-beta xylanase is classified as EC 3.2.1.8. The enzyme causes endohydrolysis of 1,4-beta-D-xylosidic linkages in xylans.

The term "family 11 xylanase" as used herein refers to an endo-1,4-beta xylanase classified as EC 3.2.1.8, which causes endohydrolysis of 1,4-beta-D-xylosidic linkages in xylans and which is classified as a family 11 xylanase according to B. Henrissat, A classification of glycosyl hydrolases based on amino acid sequence similarities. Biochem. J. 280 (1991), pp. 309-316.

In one aspect, the enzyme complex according to the invention has endo-1,4-beta xylanase activity as measured by "Assay 2" as described in the following under the heading "Assays".

"Assay 2" can be carried out at pH 3.5 or pH 5 and 50° C. using xylan as substrate, or it can be performed at different pH and temperature values for the additional characterisation and specification of enzymes. Enzyme activity is calculated from the increase in absorbance caused by xylose at 540 nm per unit time.

One unit of xylanase activity is defined herein as the amount of enzyme (normalised for total assay volume) that gives an increase in $\Delta OD_{540\ nm}\cdot min^{-1}$ under the conditions of the "Assay 2" (pH 3.5 and 50° C.).

In some embodiments the enzyme complex according to the invention comprises a xylanase activity of at least about 5000 U/g, such as at least about 6000 U/g, such as at least about 7000 U/g, such as at least about 8000 U/g, such as at least about 8500 U/g, as measured by "Assay 2".

The enzyme complex according to the invention has cellulolytic activity. The systematic name of cellulose is 4-(1,3;1,4)-β-D-glucan 4-glucanohydrolase and cellulolytic enzymes or cellulases are classified in EC 3.2.1.4. Cellulase endohydrolyse (1→4)-β-D-glucosidic linkages in e.g. cellulose, lichenin and cereal β-D-glucans and will also hydrolyse 1,4-linkages in β-D-glucans also containing 1,3-linkages. Cellulase also have other names such as endo-1,4-β-D-glucanase, β-1,4-glucanase, β-1,4-endoglucan hydrolase, cellulase A, cellulosin AP, endoglucanase D, alkali cellulose, cellulase A 3, celludextrinase, 9.5 cellulase, avicelase, pancellase SS and 1,4-(1,3;1,4)-β-D-glucan 4-glucanohydrolase.

In one aspect of the invention, the cellulase activity of the enzyme complex according to the invention is measured by "Assay 1" as described in the following under the heading "Assays".

In further aspects, the enzyme complex according to the invention has β-glucanase activity is determined as described in "Assay 7".

The standard assay is carried out at pH 5.0, and it can be performed at different pH values for the additional characterisation and specification of enzymes.

One unit of endo-1,3(4)-β-glucanase activity is defined as the amount of enzyme which produces 1 μmole glucose equivalents per minute under the conditions of the assay (pH 5.0 (or as specified) and 50° C.).

In some embodiments the enzyme complex according to the invention comprises a β-glucanase activity of at least about 10000 U/g, such as at least about 12000 U/g, such as at least about 14000 U/g, such as at least about 15000 U/g, such as at least about 18000 U/g as measured by "Assay 7".

"β-glucanase" or "beta-glucanase" as used herein refers to an endo-1,3(4)-beta-glucanase of EC 3.2.1.6. Catalyze the endohydrolysis of (1->3)- or (1->4)-linkages in beta-D-glucans when the glucose residue whose reducing group is involved in the linkage to be hydrolyzed is itself substituted at C-3.

In further aspects, the enzyme complex according to the invention has laminarinase activity is determined as described in "Assay 3".

Laminarinase may be Endo-1,3(4)-beta-glucanase classified in E.C. 3.2.1.6 or Glucan endo-1,3-beta-D-glucosidase classified in E.C. 3.2.1.39. Endo-1,3(4)-beta-glucanase with the alternative names, Laminarinase, Endo-1,3-beta-glucanase, Endo-1,4-beta-glucanase is classified in E.C. 3.2.1.6. The substrates include laminarin, lichenin and cereal D-glucans and the enzyme catalyse Endohydrolysis of (1->3)- or (1->4)-linkages in beta-D-glucans when the glucose residue whose reducing group is involved in the linkage to be hydrolyzed is itself substituted at C-3. Glucan endo-1,3-beta-D-glucosidase with the alternative names (1->3)-beta-glucan endohydrolase, Endo-1,3-beta-glucanase and Laminarinase is classified in E.C. 3.2.1.39 and hydrolyse (1->3)-beta-D-glucosidic linkages in (1->3)-beta-D-glucans in substrates as eg. laminarin, paramylon and pachyman.

In some aspects, the enzyme complex according to the invention has arabinanase activity. Arabinanase is classified as EC 3.2.1.99. The systematic name is 5-α-L-arabinan 5-α-L-arabinanohydrolase but it has several other names such as arabinan endo-1,5-α-L-arabinosidase, and endo-1, 5-α-L-arabinanase, endo-α-1,5-arabanase, endo-arabanase, 1,5-α-L-arabinan and 1,5-α-L-arabinanohydrolase. Arabinase endohydrolyses (1→5)-α-arabinofuranosidic linkages in (1→5)-arabinans. Arabinanase also acts on arabinan.

In one aspect of the invention, the arabinase activity of the enzyme complex according to the invention is measured by "Assay 4" as described in the following under the heading "Assays". The assay can be carried out at pH 3.5 and 50° C. using sugar beet arabinan as substrate, and it can be performed at different pH and temperature values for the additional characterisation and specification of enzymes. Enzyme activity is calculated from the increase in absorbance at 540 nm per unit time.

One unit of arabinase activity is defined as the amount of enzyme (normalised for total assay volume) that gives an increase in $\Delta OD_{540\ nm}\cdot min^{-1}$ under the conditions of the assay (pH 3.5 and 50° C.).

In some aspects, the enzyme complex according to the invention has beta-D-glucoside glucohydrolase activity. Beta-D-glucoside glucohydrolase refers to enzymes of E.C. 3.2.1.21.

In some aspects, the enzyme complex according to the invention has β-Xylosidase activity. "β-Xylosidase" or "Xylan 1,4-beta-xylosidase" refers to enzymes of E.C 3.2.1.37. β-Xylosidase catalyze the hydrolysis of (1->4)-beta-D-xylans, to remove successive D-xylose residues from the non-reducing termini.

In one aspect of the invention, the cellobiohydrolase activity of the enzyme complex according to the invention is measured by "Assay 6" as described in the following under the heading "Assays". The standard assay is carried out at pH 5.0, and it can be performed at different pH values for the additional characterisation and specification of enzymes.

One unit of cellobiohydrolase activity is defined as the amount of enzyme which produces 1 μmole p-nitrophenol from p-nitrophenyl β-D-cellobiopyranoside per minute under the conditions of the assay (pH 5.0 (or as specified) and 50° C.).

In some aspects, the enzyme complex according to the invention has cellobiohydrolase activity. "Cellobiohydrolase" or "Cellulose 1,4-beta-cellobiosidase" refers to enzymes of EC 3.2.1.91. Cellulose 1,4-beta-cellobiosidase catalyze hydrolysis of 1,4-beta-D-glucosidic linkages in cellulose and cellotetraose, releasing cellobiose from the non-reducing ends of the chains.

In one aspect of the invention, the arabinofuranosidase activity of the enzyme complex according to the invention is measured by "Assay 5" as described in the following under the heading "Assays". The standard assay can be carried out at pH 5.0 and 50° C. and it can be performed at different values of pH and temperature for the additional characterisation and specification of enzymes.

One unit of α-N-arabinofuranosidase activity is defined as the amount of enzyme which produces 1 µmole p-nitrophenol from p-nitrophenyl α-L-arabinofuranoside per minute under the conditions of the assay (pH 5.0 and 50° C. (or as specified)).

In some aspects, the enzyme complex according to the invention has α-N-Arabinofuranosidase activity. "α-N-Arabinofuranosidase" or "Alpha-N-arabinofuranosidase" refers to enzymes of EC 3.2.1.55. α-N-Arabinofuranosidase catalyze the hydrolysis of terminal non-reducing alpha-L-arabinofuranoside residues in alpha-L-arabinosides.

In some aspects, the enzyme complex according to the invention has glucan 1,4-beta-glucosidase activity. "Glucan 1,4-beta-glucosidase" or "glucan 1,4-beta-glucosidase" refers to enzymes of E.C.3.2.1.74. Glucan 1,4-beta-glucosidase catalyze the hydrolysis of (1->4)-linkages in (1->4)-beta-D-glucans, to remove successive glucose units.

In some aspects, the enzyme complex according to the invention has xyloglucan-specific exo-beta-1,4-glucanase activity. "xyloglucan-specific exo-beta-1,4-glucanase" refers to enzymes of E.C.3.2.1.155. Xyloglucan-specific exo-beta-1,4-glucanase catalyze the exohydrolysis of (1->4)-beta-D-glucosidic linkages in xyloglucan.

The enzyme complex according to the proceeding aspect may be used in a process comprising reducing the viscosity of an aqueous solution comprising a starch hydrolysate.

The enzyme complex may also be used in a process comprising filtering of an aqueous solution comprising a starch hydrolysate. In some embodiments the aqueous solution comprising a starch hydrolysate is a mash for beer making, and in other embodiments the aqueous solution comprising a starch hydrolysate is a food composition.

Alternatively, the enzyme complex according to the present invention may be used in the production of fruit juice, wine, grain processing, fuel alcohol, such as bioethanol, and potable alcohol.

In some embodiments the bioethanol is produced from agricultural feed stocks such as sugar cane, potato, corn, wheat sorghum etc. or from cellulosic material such as corn stover, switchgrass or other plant material. In both cases fermentable sugars are extracted from the raw material and fermented by microorganisms into alcohol, which is distilled and may be used as transportation fuel. The enzyme complex according to the present invention may be used in this production of biofuel. The enzymes complex may be added to enhance extraction of polysaccharides from the raw material, help degrade polysaccharides down into fermentable sugars and/or to enhance processing parameters such as separation of liquids from solids, flow characteristics and pumpability.

The process of the invention may be applied in the mashing of any grist. According to the invention the grist may comprise any starch and/or sugar containing plant material derivable from any plant and plant part, including tubers, roots, stems, leaves and seeds.

In some embodiments the grist comprises grain, such as grain from barley, wheat, rye, oat, corn, rice, milo, millet and sorghum, and more preferably, at least 10%, or more preferably at least 15%, even more preferably at least 25%, or most preferably at least 35%, such as at least 50%, at least 75%, at least 90% or even 100% (w/w) of the grist of the wort is derived from grain.

In some embodiments the grist comprises malted grain, such as barley malt. Preferably, at least 10%, or more preferably at least 15%, even more preferably at least 25%, or most preferably at least 35%, such as at least 50%, at least 75%, at least 90% or even 100% (w/w) of the grist of the wort is derived from malted grain.

The term "fermentation" means in the present context production of substances such as enzymes by growing microorganisms in a culture.

As used herein the term "malt" is understood as any malted cereal grain, such as barley.

The term "adjunct" is understood as the part of the grist which is not barley malt. The adjunct may be any carbohydrate rich material.

The term "mash" is understood as aqueous starch slurry, e. g. comprising crushed barley malt, crushed barley, and/or other adjunct or a combination hereof, mixed with water later to be separated into wort+spent grains.

The term "mash separation" is understood as the separation of wort from spent grains, such as by lautering or mash filtration.

The term "Beer filtration" is understood as a separation process in which the yeast cells and other turbidity-causing materials still present in the beer are removed, such as by microfiltration or membrane processes.

The enzyme complex preparation, such as in the form of a food ingredient prepared according to the present invention, may be in the form of a solution or as a solid—depending on the use and/or the mode of application and/or the mode of administration. The solid form can be either as a dried enzyme powder or as a granulated enzyme.

In one aspect the invention provides an enzyme complex preparation comprising the enzyme complex according to the invention, an enzyme carrier and optionally a stabilizer and/or a preservative.

In yet a further aspect of the invention, the enzyme carrier is selected from the group consisting of glycerol or water.

In a further aspect, the preparation comprises a stabilizer. In one aspect, the stabilizer is selected from the group consisting of inorganic salts, polyols, sugars and combinations thereof. In one aspect, the stabilizer is an inorganic salt such as potassium chloride. In another aspect, the polyol is glycerol, propylene glycol, or sorbitol. In yet another aspect, the sugar is a small-molecule carbohydrate, in particular any of several sweet-tasting ones such as glucose, fructose and saccharose.

In yet at further aspect, the preparation comprises a preservative. In one aspect, the preservative is methyl paraben, propyl paraben, benzoate, sorbate or other food approved preservatives or a mixture thereof.

Specific Embodiments of the Invention

As described above the present invention relates to an enzyme complex derived from a combination of:
  a. An expression product obtained by fermentation of a specie of the genus *Trichoderma*; and b. One or more enzymes of any one different species of the kingdom fungi selected from a xylanase (EC 3.2.1.8), a cellulase (EC 3.2.1.4), and a beta-glucanase (EC 3.2.1.6);

and wherein at least about 61% of the beta-1,4-endoglucan hydrolase activity as measured by the "Assay 1" method as described herein is derived from fermentation of the genus *Trichoderma*.

In some embodiments at least about 62%, such as at least about 63%, such as at least about 64%, such as at least about 65%, such as at least about 66%, such as at least about 68%, such as at least about 69% of the beta-1,4-endoglucan hydrolase activity as measured by the "Assay 1" method as described herein is derived from fermentation of the genus *Trichoderma*.

In some embodiments not more than about 90%, such as not more than about 85%, such as not more than about 80%, such as not more than about 75%, such as not more than about 70%, such as not more than about 65% of the beta-1,4-endoglucan hydrolase activity as measured by the "Assay 1" method as described herein is derived from fermentation of the genus *Trichoderma*.

In some embodiments the one or more enzymes of a different fungus in the enzyme complex according to the invention is an expression product obtained by fermentation of this different fungi.

In some embodiments the different fungi is of the genus *Penicillium*.

In some embodiments the expression product obtained by fermentation of the different fungi comprises a xylanase, such as a xylanase different from a xylanase derived from the genus *Trichoderma*. In some embodiments the expression product obtained by fermentation of the different fungi comprises a family 11 xylanase, such as a family 11 xylanase different from a family 11 xylanase derived from the genus *Trichoderma*.

In some embodiments the enzyme complex according to the invention comprising one or more enzyme activities selected from the list consisting of endo-1,4-β-xylanase, endo-1,3(4)-β-glucanase, cellulase, laminarinase, endo-1,5-α-L-arabinanase, beta-D-glucoside glucohydrolase, β-Xylosidase, cellobiohydrolase, glucan 1,4-beta-glucosidase, xyloglucan-specific exo-beta-1,4-glucanase and α-N-Arabinofuranosidase.

In some embodiments the expression product obtained by fermentation of a species of the genus *Trichoderma* is from one single culture of the specie *Trichoderma reesei*.

In some embodiments the expression product obtained by fermentation of a species of the genus *Penicillium* is from one single culture of the specie *Penicillium funiculosum*.

In some embodiments the single culture used for fermentation has not been genetically modified.

In some embodiments the expression product obtained by fermentation of a species of the genus *Trichoderma* is obtained by submerged fermentation.

In some embodiments the expression product obtained by fermentation of the genus *Trichoderma* is from the species *Trichoderma reesei*.

In some embodiments the expression product obtained by fermentation of a different fungus is from single culture of the species *Penicillium funiculosum*.

In some embodiments the expression product obtained by fermentation is from a wild type species.

In some embodiments the strain used for preparing the enzyme complex of the invention is *Trichoderma reesei* deposited under the Budapest treaty in the American Type Culture Collection (ATCC®) IP, Licensing and Services, 10801 University Boulevard, Manassas, Va. 20110-2209, USA having a strain designation GC Cellulose A83 GICC 0004, M03000004 and a ATCC® Patent Deposit Designation PTA-1001, on behalf of Danisco A/S on the date of 5, May 2009, or a derivative or progeny thereof. (The deposit was tested at International Depository Authority: American Type Culture Collection (ATCC®), Manassas, Va., USA on May 14, 2009 and on that date, the seeds/strain(s) were viable).

In some embodiments the strain used in preparing the enzyme complex of the invention is *Penicillium funiculosum* deposited under the Budapest treaty in the International Mycological Institute under the number IMI 378536, or a derivative or progeny thereof.

In some embodiments the enzyme complex according to the invention has an enzyme activity of at least about 3000 U/g, such as at least about 4000 U/g, such as at least about 5000 U/g, such as at least about 6000 U/g, such as at least about 7000 U/g as measured by "Assay 1" as described herein derived from fermentation of the genus *Trichoderma*.

In some embodiments the enzyme complex according to the invention has a total enzyme activity of at least about 4000 U/g, such as at least about 5000 U/g, such as at least about 6000 U/g, such as at least about 7000 U/g, such as at least about 8000 U/g, such as at least about 9000 U/g, such as at least about 10000 U/g, such as at least about 11000 U/g, such as at least about 12000 U/g, as measured by "Assay 1" as described herein.

In some embodiments the enzyme complex according to the invention consist of about 3100 u/g from *Penicillium funiculosum* and about 5200 u/g from *Trichoderma reesei* wherein said units/g is determined by "Assay 1" as described herein.

In some embodiments the enzyme complex according to the invention consist of about 2362 u/g from *Penicillium funiculosum* and about 5315 u/g from *Trichoderma reesei* wherein said units/g is determined by "Assay 1" as described herein. In some embodiments the enzyme complex according to the invention has the specifications of the "LAMINEX® XG" product as defined herein.

In yet a further aspect, the *Trichoderma reesei* strain used according to the invention has characteristics substantially identical to that of the *Trichoderma reesei* strain deposited under the Budapest treaty in the American Type Culture Collection (ATCC) having a strain designation GC Cellulose A83 GICC 0004, M03000004 deposited by Danisco A/S on the date of 5, May 2009.

In a further aspect, the strain is a *Trichoderma reesei* strain deposited under the Budapest treaty in the American Type Culture Collection (ATCC) having a strain designation GC Cellulose A83 GICC 0004, M03000004 deposited by Danisco A/S on the date of 5, May 2009.

In the context of the present invention, the phrase "characteristics substantially identical" means that the strain has one or more (preferably all) of the characteristics of the *Trichoderma reesei* deposited under the Budapest treaty in the American Type Culture Collection (ATCC), Patent Depository, 10801 University Blvd., Manassas, Va. 20110 having a strain designation GC Cellulose A83 GICC 0004, M03000004 deposited by Danisco A/S on the date of 5, May 2009.

As described above the present invention relates to the use of an enzyme complex according to the invention, in a process for production of a brewing mash, such as in the production of a malt beverage beer and/or in a whiskey production. The following embodiments are particularly relevant in the process for production of a brewing mash.

In some particular embodiments, the enzyme complex according to the present invention is not derived from a combination of an expression product obtained by fermentation of the species *Trichoderma reesei* and an expression product obtained by fermentation of the species *Penicillium funiculosum,* wherein the ratio of beta-1,4-endoglucan hydrolase activity derived from *Penicillium funiculosum* and from *Trichoderma reesei* is about 0.25/0.75 to 0.37/0.63, such as from about 0.26/0.74 to 0.36/0.64, such as from about 0.27/0.73 to 0.35/0.65, such as from about 0.28/0.72 to 0.34/0.66, such as from about 0.29/0.71 to 0.33/0.67, such as from about 0.30/0.70 to 0.32/0.68, such as from about 0.31/0.69.

In some particular embodiments, the enzyme complex according to the present invention is derived from a combination of an expression product obtained by fermentation of the species *Trichoderma reesei* and an expression product obtained by fermentation of the species *Penicillium funiculosum,* wherein the ratio of beta-1,4-endoglucan hydrolase activity derived from *Penicillium funiculosum* and from *Trichoderma reesei* is about 0.25/0.75 to 0.37/0.63, such as from about 0.26/0.74 to 0.36/0.64, such as from about 0.27/0.73 to 0.35/0.65, such as from about 0.28/0.72 to 0.34/0.66, such as from about 0.29/0.71 to 0.33/0.67, such as from about 0.30/0.70 to 0.32/0.68, such as from about 0.31/0.69.

In some embodiments the enzyme complex is used in the mash to assist in lautering and/or mash filtration and/or beer filtration.

In some embodiments the enzyme complex is used in the mash to assist in mash separation.

In some embodiments there is a reduction in wort residual β-glucan, such a reduction of at least 10%, at least 20%, or at least 30% compared to a control without enzyme, or at least 2%, 5%, or 10% compared to a control using LAMINEX® Super.

In some embodiments there is a reduced viscosity, such as wort viscosity, such as a reduction of at least 2.5%, at least 5%, or at least 7.5% compared to a control without enzyme.

In some embodiments there is an increase in brew cycles/day, such as an increase of at least 5%, such as at least 10%, or at least 20% compared to a control without enzyme, or at least 2.5%, at least 5%, or at least 10% compared to a control using LAMINEX® Super with the same or comparable enzyme activity based on the *Penicillium funiculosum* component.

In some embodiments there is enhanced filterability.

In some embodiments there is enhanced mash separation.

In some embodiments there is an increased flow rate during mash separation, such as an increase of at least 10%, at least 15%, or at least 20% compared to a control without enzyme, or at least 2.5%, at least 5%, or at least 10% compared to a control using LAMINEX® Super.

It is to be understood that the said flow rate is defined as the average flow rate calculated from the total separation time.

In some embodiments there is a decrease in sparging or extraction time, such as a decrease of at least 5%, at least 10%, at least 15%, or at least 20% compared to a control without enzyme, or a control using LAMINEX® Super.

In some embodiments there is a decrease in total lautering time.

In some embodiments there is a decreased total mash separation time, such as a decrease of at least 5%, at least 10%, or at least 15% compared to a control without enzyme, or at least 2.5%, at least 5%, or at least 10% compared to a control using LAMINEX® Super.

In some embodiments there is decreased average ΔP across the filter bed during the mash recirculation over filter bed and/or during the lautering process.

It is to be understood that ΔP refers to the pressure drop across the bed.

In some embodiments there is decreased average ΔP across the separation surface during the mash recirculation over filter bed and/or during the lautering process.

In some embodiments there is a decreased average ΔP across the separation surface during the mash separation process, such as a decrease of at least 5%, at least 10%, or at least 15% compared to a control without enzyme, or a control using LAMINEX® Super.

In some embodiments there is no change in wort haze.

In some embodiments there is there is a reduction in wort pentosans.

In some embodiments there is improved extract yield.

In some embodiments there is increased flow rate during beer filtration.

In some embodiments there is a decrease in the pressure build up across the filter over time during beer filtration, such as a decrease of at least 10%, at least 20%, or at least 25% compared to a control without enzyme, or a control using LAMINEX® Super.

In some embodiments there is decreased beer haze, such as a decrease of at least 10%, at least 20%, or at least 25% compared to a control without enzyme, or a control using LAMINEX® Super.

In some embodiments there is no decrease in foam stability.

In some embodiments there is decreased beer β-glucan, such as a decrease of at least 10%, at least 20%, or at least 25% compared to a control without enzyme, or a control using LAMINEX® Super.

In some embodiments there is a decrease in beer pentosans, such as a decrease of at least 10%, at least 20%, or at least 25% compared to a control without enzyme.

In some embodiments less than about 0.5 kg of enzyme complex per ton grist is used in a process for production of a brewing mash, such as in the production of a malt beverage beer and/or in a whiskey production. In some embodiments less than about 0.4 kg of enzyme complex per ton grist is used, such as less than about 0.3 kg of enzyme complex per ton grist is used, such as less than about 0.25 kg of enzyme complex per ton grist is used, such as less than about 0.2 kg of enzyme complex per ton grist is used, such as less than about 0.19 kg of enzyme complex per ton grist is used, such as less than about 0.18 kg of enzyme complex per ton grist, such as less than about 0.17 kg of enzyme complex per ton grist, such as less than about 0.16 kg of enzyme complex per ton grist, such as less than about 0.15 kg of enzyme complex per ton grist, such as less than about 0.14 kg of enzyme complex per ton grist, such as less than about 0.13 kg of enzyme complex per ton grist, such as less than about 0.12 kg of enzyme complex per ton grist, such as less than about 0.11 kg of enzyme complex per ton grist.

It is to be understood that a fungal strain used in accordance with the invention may be a culture of the above mentioned deposited strain, but may also be a culture of a strain which has properties substantially identical to the above mentioned isolated and deposited strain. In a preferred embodiment the strain is the deposited strain or a progeny thereof.

The expression product obtained by fermentation of a species of the genus *Trichoderma* used according to the present invention may be derived from any *Trichoderma,* such as *Trichoderma reesei,* such as the composition Celluclast® available from Novozymes A/S. Celluclast® has a pronounced viscosity-reducing effect on soluble cellulosic substrates. Alternatively LAMINEX® BG, a commercial cellulase preparation produced by *Trichoderma reesei* and available from Danisco A/S may be used.

The expression product obtained by fermentation of a species of the genus *Penicillium* used according to the present invention may be derived from any *Penicillium*, such as *Penicillium funiculosum*. In some embodiments the strain is *Penicillium funiculosum* deposited under the Budapest treaty in the International Mycological Institute under the number IMI 378536, or a derivative or progeny thereof. Alternatively the *Penicillium funiculosum* is as disclosed in WO9957325. In some alternative embodiments, LAMINEX® C2K (obtained from Danisco A/S) an expression product derived from *Penicillium funiculosum*, is used according to the invention.

LAMINEX® Super is a brewing enzyme product to be used in the mash to assist in lautering or mash filtration. The LAMINEX® Super product is a blend of two different fermentation enzyme products—the *Penicillium funiculosum* Cellulase and the *Trichoderma reesei* Cellulase. LAMINEX® Super is obtained from Danisco A/S. The *Penicillium funiculosum* component is included to hydrolyse solubilised β-glucans and xylans, reducing wort viscosity and improving lautering or mash filtration; the *Trichoderma reesei* component is included to get a low measured (by the Megazyme Mixed-linkage Beta-glucan assay procedure) β-glucan in the wort and to increase beer filtration rate.

LAMINEX® BG—*T. reesei* product(s) used to improve beer filtration obtained from Danisco A/S.

The LAMINEX® Super product is defined as being made up of:

1575 u/g (determined by "Assay 1") from *Penicillium funiculosum* concentrate;

2362 u/g (determined by "Assay 1") from *Trichoderma reesei*.

This was rounded down to 3900 u/g in the final LAMINEX® Super product specification The LAMINEX® Super specification is:

Cellulase activity≥3900 u/g (determined by "Assay 1")

pH 3.7-4.2

Micro. specs will be standard

Stabilised with 0.25% sodium benzoate.

The LAMINEX® XG is defined as being made up of:

an enzyme complex derived from a combination of an expression product obtained by fermentation of the species *Trichoderma reesei* and an expression product obtained by fermentation of the species *Penicillium funiculosum*, wherein the ratio of beta-1,4-endoglucan hydrolase activity derived from *Penicillium funiculosum* and from *Trichoderma reesei* is about 0.25/0.75 to 0.37/0.63, such as an enzyme complex wherein:

about 2363 u/g (activity measured by "Assay 1") is derived from *Penicillium funiculosum* concentrate; and about 5315 u/g (activity measured by "Assay 1") is derived from *Trichoderma reesei*. In this particular embodiment, the LAMINEX® XG product gives a *Penicillium funiculosum/Trichoderma* ration of 0.31/0.69 based on activity U as measured by "Assay 1" as described under "Assays".

EXAMPLE 1

Lab Scale Mash Study 1

Enzyme activities:

LAMINEX® Super product mixed for this specific experiment:

Nominal activity: 3937 CMC U/g. Measured activity: 3682 CMC U/g (activity measured by method "Assay 1") dosed at 0.2 kg/ton grist giving 736400 CMC U/ton grist (=0.736 U/g grist).

Giving the LAMINEX® Super product definition of 0.40×*P. funiculosum* product and 0.60×*T. reesei* product based on CMC activity as measured by "Assay 1":

activity contribution from *P. funiculosum*—0.295 CMC U/g grist activity contribution from *T. reesei*—0.442 CMC U/g grist.

LAMINEX® Super (0.200 kg/ton grist)+50% activity of the *T. reesei* component (The LAMINEX® XG):

3682 CMC U/g (activity measured by "Assay 1") dosed at 0.2 kg/ton grist+0.09534 g *T. reesei* component (12539 CMC U/g, by "Assay 1")/g LAMINEX® Super product giving 975494 CMC U/ton grist (=0.975 U/g grist)

activity contribution from *P. funiculosum*—0.295 CMC U/g grist activity contribution from *T. reesei*—(0.442+0.239) CMC U/g=0.681 CMC U/g grist.

*P. funiculosum/T. reesei* contribution ratio in The LAMINEX® XG lab scale mash study 1—0.30/0.70

Testing LAMINEX® Super (0.200 kg/ton grist) vs LAMINEX® Super (0.200 kg/ton grist)+50% activity of the *T. reesei* component in a 10% Fawcett's barley mash (90% Fawcett's malt:10% Fawcett's barley):–50 g grist in total 250 g water. Mashing profile: 50 g mixed grist ground at 0.5 mm was used and 190 ml water at 67° C. was added. The mashing temperature cycle was 60 minutes at 65° C., then 10 minutes at 72° C. The mashes were then cooled, made up to 250 g weight and filtered through fluted filter papers (Ederol 12).

Compared to the LAMINEX® Super product the enzyme solution of LAMINEX® Super (0.200 kg/ton grist) with the 50% added extra activity of the *T. reesei* component showed:

Reduced wort residual β-glucan (see FIG. 1)

Reduced wort residual β-glucan indicates a potential for reduced viscosity and following increased wort separation/filtration and a potential of increase in brew cycles/day Increased filtration (see FIG. 1)

Increased filtration indicated the positive potential of an increased length of filtration cycles without interruptions (e.g. racking) which in turn could decrease total filtration time and thus result in an increase in brew cycles/day

EXAMPLE 2

Lab Scale Mash Study 2

Enzyme activities:

LAMINEX® Super:

4380 CMC U/g (activity calculated from single component contribution) dosed at 0.2 kg/ton grist giving 876000 CMC U/ton grist (=0.876 U/g grist).

*P. funiculosum* component contributing with 2069 CMC U/g (by "Assay 1") corresponding to 0.414 CMC U/g grist.

*T. reesei* component contributing with 2311 CMC U/g (by "Assay 1") corresponding to 0.462 CMC U/g grist.

The *P. funiculosum/T. reesei* contribution ratio to the LAMINEX® Super product in this study is 0.47/0.52.

The LAMINEX® XG (LAMINEX® Super 1.5 times concentrated+an additional extra 50% activity of the *T. reesei* component):

8304 CMC U/g (activity calculated from single component contribution) dosed at 0.133 kg/ton grist giving 1104432 CMC U/ton grist (=1.104 U/g grist).

*P. funiculosum* component contributing with 3104 CMC U/g (by "Assay 1") corresponding to 0.413 CMC U/g grist

*T. reesei* component contributing with 5200 CMC U/g (by "Assay 1") corresponding to 0.692 CMC U/g grist

*P. funiculosum/T. reesei* contribution ratio in LAMINEX® XG lab scale mash study 2—0.37/0.63

Testing of LAMINEX® Super (0.200 kg/ton grist) vs LAMINEX® XG (0.133 kg/ton grist) in mixed grist— 25.8% Spitz malt and 74.2% Pilsner malt—mash. Mash profile: 50 g grist was mashed in with 150 g water and the mash program given in Table 1 was followed:

TABLE 1

Lab scale mash program:
Mashing Program

| Mashing in | at 50° C. | over 10 minutes |
|---|---|---|
| Rest | at 50° C. | for 20 minutes |
| Heating | to 65° C. | over 15 minutes |
| Rest | at 65° C. | for 30 minutes |
| Heating | to 76° C. | over 15 minutes |
| Rest | at 76° C. | for 15 minutes and then mash off |

At the end of mashing 30 ml hot water (at 76° C.) was added to each mash and the mashes were filtered hot using Ederol 12 filter papers.

Compared to the LAMINEX® Super product (dosed 0.2 kg/ton grist) the enzyme solution of LAMINEX® XG (dosed 0.133 kg/ton grist) showed:

Reduced residual wort β-glucan concentrations (see FIG. 2)

The importance of reducing the wort β-glucan concentration is not clear, however theories associate reduced wort β-glucan with reduced wort viscosities. With mash separation as the bottleneck of the brewing process the resulting positive increase could increase brew house capacity by increasing number of brew cycles/day due to the decreased time spent on mash separation.

Increased filtration volumes over time (see FIG. 2)

Higher filtration rates positively decreases time spent on filtration, potentially resulting in an increase in brew house capacity by increasing the number of brew cycles/day.

Reduced wort viscosity (see FIG. 2)

Reduced wort viscosity has the positive potential of increasing filtration rates and thus increasing brew house capacity.

EXAMPLE 3

Pilot Brewery Trials

Same enzyme compositions as in lab scale mash study 2.

Testing The LAMINEX® Super (0.200 kg/ton grist equivalent) and LAMINEX® XG (LAMINEX® Super 1.5 times concentrated+an additional 50% extra activity if the *T. reesei* component) (0.133 kg/ton grist). The pilot brewery mashing study was conducted using 31 kg mixed grist— 25.8% Spitz malt and 74.2% Pilsner malt—in a mash volume of 110 L. Mashing profile is seen in Table 2.

TABLE 2

Pilot brewery mashing profile:

| Step | Time (min.) | Total time (min.) | Temperature (deg C.) |
|---|---|---|---|
|  | 0 | 0 | 50 |
| Mashing in | 10 | 10 | 50 |
| Rest | 20 | 30 | 50 |
| Heating | 15 | 45 | 65 |
| Rest | 30 | 75 | 65 |
| Heating | 15 | 90 | 76 |
| Rest | 15 | 105 | 76 |

Pilot Brewery Mashing Trials

In comparison to LAMINEX® Super addition of LAMINEX® XG in the mashing process results in:

Decreased sparging time by up to 13% (see Table 3)

Decreased sparging time contributes positively to a decreased time spent on wort separation and thus is a potential for increased brewhouse capacity by an increase in number of brew cycles/day.

Decreased total lautering time by up to 8% as compared to LAMINEX® Super and up to 20% as compared to water control (no enzyme added) (see Table 3 and FIG. 3).

With the lautering process being the bottleneck of the brewing process, decreasing lautering time has the potential of boosting the brewhouse capacity by increasing the number of brew cycles/day.

increased average flow rate either calculated as the average of the flow rates measure "continuously" during the lautering process or as the "Total volume filtered" per the "Total time of lautering" (see Table 3 and FIG. 3).

Increased average flow rate could positively decrease total time spent on wort separation and thus potentially increase brew house capacity.

decreased average ΔP across the filter bed by up to 19% during the lautering process (see Table 3).

Potentially, a decreased average ΔP across the filter bed could result in a decreased need for filter bed racking and increase volume filtered over time. Both factors have the positive potential of decreasing lautering time and thus increasing brew house capacity decreased pressure build up during the mash recirculation over filter bed (by up to 22%) and during lautering (by up to 24%) (see Table 3)

Both decreased pressure build during recirculation and lautering have the potential of contributing to increased filtration and thus decreased total lautering time. Again this could result in increased brew house capacity. The effect seen is especially strong as an increased rate of filtration would normally be linked to an increase in pressure—and the present data show increase in filtration and at the same a decrease pressure build up.

no change in wort haze (see Table 3)

That haze is unchanged, which is positive as an increased haze could be a factor resulting in the choice of induction of raking. Racking is time consuming and would increase total time of wort separation and thus decreased brew house capacity.

decreased "total pressure build up" during lautering by up to 24% (see Table 3 and FIG. 3).

Decreased "total pressure build up" during wort separation would increase filtration rate and thus increased brew house capacity by decreased time spent on the wort separation process.

absence of filter bed racking induced by pressure build up. As marked by (1) in bottom of see Table 3 only the obligatory racking was introduced when including the LAMINEX® XG at the mashing step (marked by (1) in Table 3).

Decreasing the sparging time contributes to decrease in total lautering time and a potential increase in the number of brew cycles/day.

TABLE 3

Pilot brewery mashing trials - summary of lautering data

|  |  | Control | LAMINEX® Super | LAMINEX® XG |
|---|---|---|---|---|
| Date |  | 16-Oct-08 | 21-Oct-08 | 28-Oct-08 |
| Brew no.: |  | 73 | 75 | 79 |
| Pilsner malt | (kg) | 23.0 | 23.0 | 23.0 |
| Spitz malt | (kg) | 8.0 | 8.0 | 8.0 |
| Total Grist | (kg) | 31.0 | 31.0 | 31.0 |
| Time first wort | (min.) | 35.50 | 25.00 | 25.50 |
| Time 1st Sparging | (min.) | 8.00 | 7.50 | 7.50 |
| Time 2nd Sparging | (min.) | 6.00 | 17.00 | 11.17 |
| Time 3rd Sparging | (min.) | 16.50 | 6.00 | 5.83 |
| Time 4th Sparging | (min.) | 6.50 | 6.00 | 6.00 |
| Time 5th Sparging | (min.) | 7.50 | 8.00 | 8.17 |
| Time Spargings | (min.) | 44.50 | 44.50 | 38.67 |
| Total Lautering Time | (min.) | 80.00 | 69.50 | 64.17 |
| Average flow rate | (l/h) | 126.3 | 136.8 | 139.4 |
| Average flow rate* | (l/h) | 111.8 | 128.6 | 139.3 |
| Average ΔP | (barg) | 169 | 179 | 145 |
| P build up - recirculation | (barg) | 104 | 93 | 73 |
| P build up - lautering | (barg) | 555 | 396 | 300 |
| P build up - total | (barg) | 659 | 489 | 373 |
| Rakings ($1^{st}$ wort + spargings)** |  | 1 + 1 | 0 + 1 | 0 + (1) |

*From total volume and total lautering time
**1 means raking induced by pressure increase, 0 means no raking, (1) means obligatory raking manually induced at the beginning of 2nd sparging if there was none before.

Wort sample analyses of mashes added the LAMINEX® XG in the mashing process results in:
  decreased wort β-glucan as measured by the Megazyme Mixed Linkage Beta-Glucan Method (Megazyme catalogue reference K-BGLU complying with standard AOAC Method 995.16) (see Table 4).

Decreased wort residual β-glucan could result in a positive decrease in wort viscosity, thus increasing filtration and brew house capacity by increasing the number of brew cycles/day.
  increased extract by up to 2.3% (see Table 4).

An increase in extract would give a positive increase in brew house yield—more product produced from the same amount of raw material—in other terms an increased brew house capacity in a more cost efficient way.

TABLE 4

Pilot brewery wort analyses:

| Trial no. | Sample | Extract (° P) | [β-Glucan] (mg/l) |
|---|---|---|---|
| 73 | Combined wort | 14.11 | 1163 |
| 75 | Combined wort | 14.18 | 588 |
| 79 | Combined wort | 14.34 | 187 |

73: Negative control: No enzyme control
75: LAMINEX® Super at 0.20 kg/ton
79: LAMINEX® XG at 0.133 kg/ton Pilot Brewery Beer Filtration In comparison to LAMINEX® Super addition of the LAMINEX® XG in the mashing process results in:
  Increased flow rate during beer filtration (see Table 5).
  Increased flow rate during beer filtration has the positive effect of increasing filtration capacity and thus potentially decrease (limit) the needs for extra bright beer tank (BBT) capacity (BBT are pressure tanks used for beer storage after filtration until filling. These tanks are able to keep a stable pressure, avoid loss of carbon dioxide and prevent the formation of foam).
  Significantly decrease in pressure build up across filter over time (see Table 5).
  Decrease in pressure build up across filter over time positively increases the length of the filtration cycle between cleaning. This positively limits cleaning in place, the water and energy consumption. Also the amount filter material needed is decreased resulting in cost savings. Longer filtration cycles between cleaning positively reduce the loss of beer coming from start up and stop of beer filtration process.

TABLE 5

Summary of pilot brewery beer filtration data:

| 73 | | | 75 | | | 79 | | |
|---|---|---|---|---|---|---|---|---|
| Volume (l) | Flow (l/h) | ΔP (barg) | Volume (l) | Flow (l/h) | ΔP (barg) | Volume (l) | Flow (l/h) | ΔP (barg) |
| 0.0 | 95.0 | 1.90 | 0.0 | 106.0 | 1.70 | 0.0 | 130.0 | 1.00 |
| 2.0 | 60.0 | 4.20 | 5.0 | 115.0 | 2.60 | 5.0 | 120.0 | 1.00 |
| 3.0 | 125.0 | 2.30 | 10.0 | 123.0 | 3.20 | 10.0 | 116.0 | 0.80 |
| 7.0 | 115.0 | 2.50 | 15.0 | 118.0 | 3.50 | 14.0 | 116.0 | 1.40 |
| 11.0 | 109.0 | 4.20 | 20.0 | 119.0 | 3.90 | 18.0 | 119.0 | 1.60 |
| 15.0 | 81.0 | 4.10 | 25.0 | 116.0 | 4.20 | 22.0 | 118.0 | 1.85 |
| 20.0 | 64.0 | 4.10 | 30.0 | 105.0 | 4.30 | 26.0 | 119.0 | 2.10 |
| 25.0 | 52.0 | 4.10 | 35.0 | 99.0 | 4.30 | 30.0 | 119.0 | 2.20 |
| 30.0 | 22.0 | 4.20 | 40.0 | 92.0 | 4.20 | 34.0 | 120.0 | 2.30 |
| 32.0 | 8.0 | 4.20 |  |  |  | 38.0 | 118.0 | 2.45 |
| 33.0 | 0.0 | 4.20 |  |  |  | 42.0 | 117.0 | 2.60 |
|  |  |  |  |  |  | 44.0 | 117.0 | 2.75 |

73: Negative control: No enzyme control
75: LAMINEX® Super at 0.20 kg/ton
79: LAMINEX® XG at 0.133 kg/ton Pilot Brewery Beer Analyses Analyses of beer produced from mashes added the LAMINEX® XG in the mashing process show:
  decreased beer beta-glucan (see Table 6)
  Decreased beer β-Glucan could positively decrease beer viscosity and thereby increase the filtration cycle and reduce the filter aid and utility consumption (cost saving).
  Decreased beer haze (see Table 6).
  The major contributor to beer haze can be related to non beta-glucan material. Reduced beer β-glucan could also contribute positively to decreased beer haze, giving a positive appearance of the beer.

No decrease in foam stability (see Table 6—Head retention value)

Beer foam stability was not decreased using the "LAMINEX® Super 1.5 times conc+additional 50% extra activity of the *T. reesei* component". This is positive as it would be a compromising factor in regard to beer appearance and quality.

Decreased beer pentosans could be expected

Decreased beer pentosans could contribute positively to increased beer filtration

TABLE 6

Pilot brewery beer analyses:

|  |  | 73 Control | 75 Standard | 79 Test |
|---|---|---|---|---|
| Specific Gravity |  | 1.0101 | 1.0114 | 1.0111 |
| [β-Glucan] | (mg/l) | 389 | 209 | 133 |
| Haze: Radiometer | (EBC) | 2.70 | 1.55 | 1.00 |
| Haze: Hach | (EBC) | 2.40 | 1.13 | 0.68 |
| Head Retention Value | (s) | 90 | 108 | 136 |
| Forced Ageing Test | (EBC) | 1.80 | 0.25 | 0.20 |

73: Negative control: No enzyme control
75: LAMINEX ® Super at 0.20 kg/ton
79: LAMINEX ® XG at 0.133 kg/ton

EXAMPLE 4

Full Scale Brewery Studies.

Line 1 Trial:

Trial was running on a 31.6% Barley grist composition using 9500 kg of grist per brew (3000 kg Barley, 6500 kg Malt).

As demonstrated by table 7, good results were observed with LAMINEX® XG with respect to mash separation. Decreasing lautering time has the potential of boosting the brewhouse capacity by increasing the number of brew cycles/day.

TABLE 7

Brewhouse performance on Mash separation.

|  |  | BREW HOUSE | |
|---|---|---|---|
| LAMINEX ® | kg/brew | Mash separation time, AU | Total mash separation time, AU |
| I - Control |  |  |  |
| Super | 2 | 100 | 129 |
| Super | 2 | 108 | 100 |
| II - Test |  |  |  |
| XG | 1.4 | 93 | 86 |
| XG | 1.4 | 94 | 87 |

AU—Arbitrary Unit

Line 2 Trial:

Trial was running on a 28% Barley grist composition using 12300 kg of grist per brew (3500 kg Barley, 8800 kg Malt).

As demonstrated by Table 8, good results were observed with LAMINEX® XG with respect to Beer filtration.

Increasing beer filtration cycles between cleaning has the potential of boosting the brewhouse capacity by decreasing the time spent on cleaning and increasing the number of beer filtration brew cycles/day. Also, increasing beer filtration cycles result in cost saving and reduced energy consumption and reduced the loss of beer coming from start up and stop of beer filtration. Reduce the filter aid and utility consumption (reduced kieselguhr consumption) result in a direct cost saving.

TABLE 8

Brewhouse performance on Beer filtration.

|  |  | BEER FILTRATION | |
|---|---|---|---|
| LAMINEX ® | kg/brew | Filtration cycle, AU | Kiselgur consumption, AU |
| I - Control |  |  |  |
| Super | 2 | 100 | 100 |
| II - Test |  |  |  |
| XG | 1.4 | 148 | 48 |
| XG | 1.4 | 138 | 76 |

AU—Arbitrary Unit

As presented in Table 9 analyses of beer produced from Line 2 added the LAMINEX® XG in the mashing process showed: Decreased beer beta-glucan.

Decreased beer β-Glucan could positively decrease beer viscosity and thereby increase the filtration cycle and reduce the filter aid and utility consumption (cost saving).

Reduced beer pentosans could be expected.

Decreased beer pentosans could contribute positively to increased beer filtration by reducing viscosity.

Reduced beer dynamic viscosity

Reduced beer viscosity could positively increase filtration cycles and reduce the filter aid and utility consumption (cost saving). Increased filtration cycles could also increase brew house capacity by increasing number of beer filtration cycles/day

TABLE 9

Full scale brewery beer analyses, Line 2

| Analyses (Arbitrary units) | LAMINEX ® Super - 0.163 kg/ton grist | LAMINEX ® Super XG - 0.113 kg/ton grist |
|---|---|---|
| Dyn. Visc. (70.00°) | 100 | 95.7 |
| β-Glucan | 100 | 3.30 |

Summary—Enzyme Activity Dosing used in Trials

Data is given in the PF/TR ratio which is just the ratio of contribution from each component to the total activity. PF is the contribution made by *Penicillium funiculosum* and TR the contribution made by *Trichoderma reesei*.

TABLE 10

Enzyme CMC activities used in the different trials/examples.

|  | LAMINEX ® Super PF/TR ratio | LAMINEX ® XG PF/TR ratio |
|---|---|---|
| Lab scale mash study 1 | 0.4/0.6 | 0.30/0.70 |
| Lab scale mash study 2 | 0.47/0.52 | 0.37/0.63 |
| Pilot brewery Study | 0.47/0.52 | 0.37/0.63 |
| Full scale brewery study, Line 1 | 0.4/0.6 | 0.31/0.69 |
| Full scale brewery study, Line 2 | 0.4/0.6 | 0.31/0.69 |

Assays

Assay 1: DNS Cellulase Activity Method (DNS CMC Method)

Systematic Name: 1,4-(1,3;1,4)-β-D-glucan 4-glucanohydrolase

IUB Number: EC 3.2.1.4

Principle

The assay of cellulase is based on the enzymatic endo-hydrolysis of the 1,4-β-D-glucosidic bonds in carboxymethylcellulose (CMC), a β-1,4-glucan. The products of the reaction (β-1,4 glucan oligosaccharides) was determined colorimetrically by measuring the resulting increase in reducing groups using a 3,5-dinitrosalicylic acid reagent. Enzyme activity was calculated from the relationship between the concentration of reducing groups, as glucose equivalents, and absorbance at 540 nm.

The assay was carried out at pH 5.0, but it can be performed at different pH values for the additional characterisation and specification of enzymes.

Unit Definition

One unit of cellulase activity is defined as the amount of enzyme which produces 1 μmole glucose equivalents per minute under the conditions of the assay (pH 5.0 (or as specified) and 50° C.).

Materials

Carboxymethylcellulose. Supplier: Megazyme Ltd. Product no.: CM-Cellulose 4M

D-Glucose 'AnalaR'. Supplier: Merck Ltd (BDH). Product no.: 10117. M.W.: 180.16

Sodium acetate anhydrous 'AnalaR'. Supplier: Merck Ltd (BDH). Product no.: 10236. M.W.: 82.03

Acetic acid ("glacial") 'AnalaR'. Supplier: Merck Ltd (BDH). Product no.: 10001. M.W.: 60.05

3,5-Dinitrosalicylic acid GPR (3,5-dinitro-2-hydroxybenzoic acid). Supplier: Merck Ltd (BDH). Product no.: 28235

Sodium hydroxide pellets 'AnalaR'. Supplier: Merck Ltd (BDH). Product no.: 10252. M.W.: 40.00

Potassium sodium (+)-tartrate 'AnalaR'. Supplier: Merck Ltd (BDH). Product no.: 10219. M.W.: 282.22

1.5% (w/v solution) Carboxymethylcellulose (CMC) solution in 0.1M sodium acetate buffer, pH 5.0 (substrate solution).

3,5-Dinitrosalicylic acid (DNS) solution. 20 g/L of DNS in buffer containing 32 g/L sodium hydroxide pellets, and 600 g/L potassium sodium (+)-tartrate.

Glucose standard solution (0.50 mg/ml)

Procedure

The enzyme complex was diluted into samples and a glucose standard curve as shown in FIG. 2 was made using glucose concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. This is followed by heating to 95° C. for 5 minutes.

The optical density was measured at 540 nm ($OD_{540\ nm}$) of the different samples.

Calculation

The enzyme activity is determined from the standard curve as shown in FIG. 2.

The activity is calculated as follows:

$$\text{Activity}\ (u.ml^{-1}\ \text{or}\ u.g^{-1}) = \frac{T-c}{m} \times A \times \frac{1}{180.16} \times 10^3 \times \frac{1}{V} \times \frac{1}{t} \times D$$

where:

$T = \Delta OD_{540nm}\text{TEST}$ $\quad = OD_{540nm}\text{TEST} - OD_{540nm}\text{BLANK}$ $m$ = gradient of the standard curve (approximately 1.0)

$c$ = y axis intercept of the standard curve (always negative and approximately −0.02)

$180.16 \equiv$ molecular weight of glucose $10^3 \equiv$ to convert to μmoles $A \equiv$ assay volume in ml $V \equiv$ enzyme volume in ml $t \equiv$ assay time in minutes $D$ = actual enzyme dilution factor (e.g. for 1.000 g diluted to 1 litre $D = 1000$)

Assay 2. Endo-1,4-β-Xylanase (DNS Birchwood Xylan Method)

Principle

The reaction, catalysed by endo-1,4-β-xylanase, involves the endohydrolysis of the 1,4-β-D-xylosidic bonds in xylan (e.g. birchwood xylan or cereal substituted xylans such as wheat arabinoxylan) forming β-1,4 xylan oligosaccharides.

The products of the reaction (β-1,4-xylan oligosaccharides) was determined colorimetrically by measuring the resulting increase in reducing groups using a 3,5-dinitrosalicylic acid reagent. Enzyme activity is calculated from the relationship between the concentration of reducing groups, as xylose equivalents, and absorbance at 540 nm.

The standard assay was carried out at pH 3.5, but it can be performed at different pH values for the additional characterisation and specification of enzymes.

Unit Definition

One unit of endo-1,4-β-xylanase activity is defined as the amount of enzyme which produces 1 μmole xylose equivalents per minute under the conditions of the assay (pH 3.5 (or as specified) and 50° C.).

Materials:

See the list of materials given above for the Cellulase activity assay.

Birchwood xylan. Supplier: Sigma Chemical Co. Product no.: X 0502

D(+)-Xylose 'AnalaR'. Supplier: Merck Ltd (BDH). Product no.: 10372 M.W.: 150.13

1.5% (w/v solution) Birchwood xylan solution in 0.1 sodium acetate buffer, pH 4.0 (substrate solution)

Xylose standard solution (0.50 mg/ml)

Procedure 1.75 ml birchwood xylan solution was mixed with 0.25 ml diluted enzyme solution at 50° C. for 10 minutes, the reaction was stopped by addition of 2 ml DNS solution, followed by heating to 95° C. for 5 minutes. Optical density was measured at 540 nm ($OD_{540\ nm}$).

A standard curve was made from 0.125, 0.250, 0.375, 0.500 mg/ml xylose

Calculation

The activity is calculated as follows:

$$\text{Activity } (u.\text{ml}^{-1} \text{ or } u.\text{g}^{-1}) = \frac{T-c}{m} \times A \times \frac{1}{150.13} \times 10^3 \times \frac{1}{V} \times \frac{1}{t} \times D$$

where:

$T = \Delta OD_{540nm}\text{TEST}$ $= OD_{540nm}\text{TEST} - OD_{540nm}\text{BLANK}$ $m$ = gradient of the standard curve (approximately 1.0)

$c$ = y axis intercept of the standard curve (always negative and approximately −0.02)

$150.13 \equiv$ molecular weight of xylose $10^3 \equiv$ to convert to $\mu$moles $A \equiv$ assay volume in ml $V \equiv$ enzyme volume in ml $t \equiv$ assay time in minutes $D$ = actual enzyme dilution factor (e.g. for 1.000 g diluted to 1 litre $D = 1000$)

Assay 3. Laminarinase (DNS Laminarin Method)

Principle

The reaction, catalysed by laminarinase, involves the endohydrolysis of 1,3-glucosidic bonds in 1,3-β-D-glucans. Substrates include laminarin, paramylon and pachyman. The products of the reaction (β-1,3-glucan oligosaccharides) are determined colourimetrically by measuring the resulting increase in reducing groups using a 3,5-dinitrosalicylic acid reagent. Enzyme activity is calculated from the relationship between the concentration of reducing groups, as glucose equivalents, and absorbance at 540 nm.

The assay was carried out at pH 5.0 and 50° C., but it can be performed at different values of pH and temperature for the additional characterisation and specification of enzymes.

Unit Definition

One unit of laminarinase activity is defined as the amount of enzyme which produces 1 μmole glucose equivalents per minute under the conditions of the assay (pH 5.0 and 50° C. (or as specified)).

Materials

See materials given above for the Cellulase activity assay.

Laminarin (from *Laminaria digitata*). Supplier: Sigma-Aldrich Co. Ltd. Product no.: L 9634

1.00% (w/v solution) Laminarin solution (substrate solution 0.1M sodium acetate buffer, pH 5.0)

1.75 ml laminarin solution is mixed with 0.25 ml diluted enzyme solution at 50° C. for 10 minutes and the reaction stopped by addition of 2 ml DNS solution.

Standard curve was made using 0, 0.125, 0.25, 0.5 and 0.75 mg/ml glucose solution.

Optical density was measured at 540 nm ($OD_{540\ nm}$).

Calculation

The activity is calculated as follows:

$$\text{Activity } (u.\text{ml}^{-1} \text{ or } u.\text{g}^{-1}) = \frac{T-c}{m} \times A \times \frac{1}{180.16} \times 10^3 \times \frac{1}{V} \times \frac{1}{t} \times D$$

where:

$T = \Delta OD_{540nm}\text{TEST}$ $= OD_{540nm}\text{TEST} - OD_{540nm}\text{BLANK}$ $m$ = gradient of the standard curve (approximately 1.0)

$c$ = y axis intercept of the standard curve (always negative and approximately −0.03)

$180.16 \equiv$ molecular weight of glucose $10^3 \equiv$ to convert to $\mu$moles $A \equiv$ assay volume in ml $V \equiv$ enzyme volume in ml $t \equiv$ assay time in minutes $D$ = enzyme dilution factor (e.g. for 1 g diluted to 1 litre $D = 1000$)

Assay 4. Arabinase Assay.

Principle

The assay of Arabinase activity is based on colorimetrically determination by measuring the resulting increase in reducing groups using a 3,5-dinitrosalicylic acid reagent. Enzyme activity was calculated from the relationship between the concentration of reducing groups, as arabinose equivalents, and absorbance at 540 nm.

The assay was carried out at pH 3.5, but it can be performed at different pH values for the additional characterisation and specification of enzymes.

Unit Definition

One unit of arabinase (Arabinanase (endo-1,5-alpha-L-arabinanase)) activity is defined as the amount of enzyme which produces 1 μmole arabinose equivalents per minute under the conditions of the assay (pH 3.5 (or as specified) and 50° C.).

Materials

Megazyme Sugar Beet Arabinan

Arabinose Sigma A3131 M.W.: 150.1

Sodium acetate anhydrous 'AnalaR'. Supplier: Merck Ltd (BDH). Product no.: 10236. M.W.: 82.03

Acetic acid ("glacial") 'AnalaR'. Supplier: Merck Ltd (BDH). Product no.: 10001. M.W.: 60.05

3,5-Dinitrosalicylic acid GPR (3,5-dinitro-2-hydroxybenzoic acid). Supplier: Merck Ltd (BDH). Product no.: 28235

Sodium hydroxide pellets 'AnalaR'. Supplier: Merck Ltd (BDH). Product no.: 10252. M.W.: 40.00

Potassium sodium (+)-tartrate 'AnalaR'. Supplier: Merck Ltd (BDH). Product no.: 10219. M.W.: 282.22

1.5% (w/v solution) Arabinan solution in 0.1M sodium acetate buffer, pH 3.5 (substrate solution).

3,5-Dinitrosalicylic acid (DNS) solution. 20 g/L of DNS in buffer containing 32 g/L sodium hydroxide pellets, and 600 g/L potassium sodium (+)-tartrate.

Arabinase standard solution (0.50 mg/ml)

Procedure

The enzyme complex was diluted into samples and a glucose standard curve was made using arabinase concentrations of 0, 0.125, 0.25, 0.375, and 0.5 mg/ml.

0.25 ml of enzyme solution was mixed with 1.75 ml of the substrate solution (1.5% w/v) at 50° C. and the reaction was stopped after 10 min by addition of DNS solution. Followed by heating to 95° C. for 5 minutes.

The optical density was measured at 540 nm ($OD_{540\ nm}$) of the different samples.

Calculation

The enzyme activity is determined from the standard curve.

The activity is calculated as follows:

$$\text{Activity}\ (u.ml^{-1}\ \text{or}\ u.g^{-1}) = \frac{T-c}{m} \times A \times \frac{1}{150.13} \times 10^3 \times \frac{1}{V} \times \frac{1}{t} \times D$$

where:

$T = \Delta OD_{540nm}\text{TEST}$
$\quad = OD_{540nm}\text{TEST} - OD_{540nm}\text{BLANK}$ $m$ = gradient of the standard curve (approximately 1.0)

$c$ = y axis intercept curve of the standard curve (always negative and approximately −0.02)

150.13 ≡ molecular weight of arabinase $10^3$ ≡ to convert to $\mu$molees $A$ ≡ assay volume in ml $V$ ≡ enzyme volume in ml $t$ ≡ assay time in mintues $D$ = actual enzyme dilution factor (e.g. for 1.000 g diluted to 1 litre $D$ = 1000)

Assay 5. Arabinofuranosidase Assay.

The reaction, catalysed by α-N-arabinofuranosidase, involves the hydrolysis of the terminal bond, at the non-reducing α-L-arabinofuranoside residue, of α-L-arabinosides. The enzyme acts on α-L-arabinofuranosides, α-L-arabinans containing (1,3)- and/or (1,5)-linkages, arabinoxylans and arabinogalactans.

The assay of α-N-arabinofuranosidase is based upon the enzymatic hydrolysis of p-nitrophenyl α-L-arabinofuranoside. The assay is a "two-point", rather than a "continuous monitoring", method. The calculation of enzyme activity is based on measurements taken only at the beginning and end of the incubation period. A product of the reaction, p-nitrophenol is determined colourimetrically (after pH adjustment). Enzyme activity is calculated from the relationship between the concentration of p-nitrophenol and absorbance at 400 nm.

Preparation of Diluted Enzyme Solution:

Prepare all enzyme solutions, from powder or liquid enzyme preparations, with glass distilled water. Minimise assay dilution errors by avoiding large dilution steps involving small volumes or weights. In making enzyme dilutions it is more accurate, even for a liquid sample, to weigh out the initial enzyme sample. If this is done, in the case of liquid samples it is therefore necessary to measure the specific gravity of the liquid at 20° C.

As the assay is a "two-point", rather than a "continuous monitoring", method it is important to ensure the linearity within the incubation period with different enzyme systems and conditions. Under the standard assay conditions of substrate concentration, pH, temperature and assay time the assay has been demonstrated to be linear in the range $\Delta OD_{540\ nm}$ TEST (T)=0.20–1.50. However, for good practice, the assay is operated within a defined range of $\Delta OD_{540\ nm}$ TEST (T)=0.400–0.800.

Procedure

Each enzyme sample assay involves three analyses: duplicate test (TEST) analyses and a blank (BLANK) analysis. The procedure given describes the analysis of a single enzyme sample.

|  | TEST | BLANK |
|---|---|---|
| 0.2M Sodium acetate buffer, pH 5.0 | 1.00 ml | 1.00 ml |
| Glass distilled water | 1.00 ml | 1.00 ml |
| p-Nitrophenyl-α-L-arabinofuranoside solution | 1.00 ml | 1.00 ml |

0.25 ml diluted enzyme solution was added to the solutions at 50° C., the reaction was stopped after 10 minutes by addition of 4 ml of 0.4M glycine solution, pH 10.8 (stop reagent).

Absorbance was measured at 400 nm at 25° C. against a water blank.

determine $OD_{400\ nm}$ TEST for the duplicate TESTS measured;

determine $OD_{400\ nm}$ BLANK.

Calculation $$\Delta OD_{400nm}\text{TEST}(T) = OD_{400nm}\text{TEST} - OD_{400nm}\text{BLANK}$$

$$\text{Units}\ (\mu mol.min^{-1}) = \frac{T}{18300} \times \frac{V}{1000} \times 10^6 \times \frac{1}{t}$$

$$\text{Activity}\ (u.ml^{-1}\ \text{or}\ u.g^{-1}) = \text{Units} \times \frac{1}{E} \times D$$

where: T=OD400 nm TEST−OD400 nm BLANK

18300=Molar extinction coefficient for p-nitrophenol (1 cm path length)

V=7.25 (total liquid volume in test in ml)

t=10 (minutes)

1 u=1 μmol.min-1

E=0.25 (volume of diluted enzyme sample in ml)

D=Enzyme dilution factor e.g. for 1 ml diluted to 1 litre D=1000)

Assay 6. Cellobiohydrolase Assay.

Principle

The reaction, catalysed by cellobiohydrolase, involves the hydrolysis of 1,4-β-D-glucosidic linkages in cellulose and cellotetraose, releasing cellobiose from the non-reducing ends of the chains.

The assay of cellobiohydrolase is based on the enzymatic hydrolysis of p-nitrophenyl β-D-cellobiopyranoside. The product of the reaction, p-nitrophenol is determined colorimetrically (after pH adjustment). Enzyme activity is calculated from the relationship between the concentration of p-nitrophenol and absorbance at 400 nm.

The assay is operated within the linear defined range of $\Delta OD_{540\ nm}$ TEST (T)=0.400–0.800.

Procedure

Each enzyme sample assay involves three analyses: duplicate test (TEST) analyses and a blank (BLANK) analysis. The procedure given describes the analysis of a single enzyme sample.

|  | TEST | BLANK |
|---|---|---|
| 0.2M Sodium acetate buffer, pH 5.0 | 1.00 ml | 1.00 ml |
| Glass distilled water | 1.00 ml | 1.00 ml |
| p-Nitrophenyl β-D-cellobiopyranoside solution | 1.00 ml | 1.00 ml |

0.25 ml diluted enzyme solution was added to the test solution at 50° C., after 30 minutes 4 ml of 0.4M glycine solution, pH 10.8 (stop reagent) was added to each tube.

Absorbance was measured at 20° C. at 400 nm in a 1 cm glass cuvette against a water blank.
determine OD400 nm TEST for the duplicate TESTS measured;
determine OD400 nm BLANK.

Calculation $$\Delta OD_{400nm} \text{TEST}(T) = OD_{400nm}\text{TEST} - OD_{400nm}\text{BLANK}$$

$$\text{Units } (\mu mol.min^{-1}) = \frac{T}{18300} \times \frac{V}{1000} \times 10^6 \times \frac{1}{t}$$

$$\text{Activity } (u.mol^{-1} \text{ or } u.g^{-1}) = \text{Units} \times \frac{1}{E} \times D$$

where: T=OD$_{400\,nm}$ TEST−OD$_{400\,nm}$ BLANK
18300=Molar extinction coefficient for p-nitrophenol (1 cm path length)
V=7.25 (total liquid volume in test in ml)
1000=to convert to litres
$10^6$=to convert to μmoles
t=30 (minutes)
1 u=1 μmol.min$^{-1}$
E=0.25 (volume of diluted enzyme sample in ml)
D=Enzyme dilution factor e.g. for 1 ml diluted to 1 litre D=1000)

Assay 7. β-Glucanase Assay.
Principle

The reaction, catalysed by endo-1,3(4)-β-glucanase, involves the endohydrolysis of 1,3- or 1,4-glucosidic bonds in β-D-glucans when the glucose residue, whose reducing group is involved in the bond to be hydrolysed, is itself substituted at C-3. Substrates include cereal β-D-glucans, laminarin and lichenin. By definition this enzyme is different from EC 3.2.1.39 (endo-1,3-β-glucanase, or laminarinase).

The assay of endo-1,3(4)-β-glucanase is based on the enzymatic hydrolysis of the 1,3- or 1,4-glucosidic bonds in barley β-glucan, a β-1,3(4)-glucan. The products of the reaction (β-1,3(4)-glucan oligosaccharides) are determined colourimetrically by measuring the resulting increase in reducing groups using a 3,5-dinitrosalicylic acid reagent. Enzyme activity is calculated from the relationship between the concentration of reducing groups, as glucose equivalents, and absorbance at 540 nm.

In this assay after the addition and mixing of the DNS reagent the assay tubes are put into a boiling water bath (95° C. minimum) and incubated for exactly 15 minutes. This is in contrast to DNS based enzyme assays with other substrates in which the incubation period is 5 minutes. This change also affects the range of $\Delta OD_{540\,nm}$ TEST (T) values that are acceptable in the test.

Whilst the standard assay is carried out at pH 5.0, it can be performed at different pH values for the additional characterisation and specification of enzymes. In this case only the pH of the buffer solutions (noted below) is changed.

Reagents Required

In all cases, except for the Beta-glucan, it is the identity and purity of the reagents, and not the supplier, which are important.

Beta-glucan (Barley; medium viscosity), Megazyme Ltd, Product no. P-BGBM, Viscosity: 20-30 cSt
D-Glucose 'AnalaR', Merck Ltd (BDH), Product no. 10117, M.W.: 180.16
Sodium acetate anhydrous 'AnalaR', Merck Ltd (BDH), Product no. 10236, M.W. 82.03
Acetic acid ("glacial") 'AnalaR', Merck Ltd (BDH), Product no. 10001, M.W. 60.05
3,5-Dinitrosalicylic acid GPR (3,5-dinitro-2-hydroxybenzoic acid), Merck Ltd (BDH), Product no. 28235,
Sodium hydroxide pellets 'AnalaR', Merck Ltd (BDH), Product no. 10252, M.W. 40.00
Potassium sodium (+)-tartrate 'AnalaR', Merck Ltd (BDH), Product no. 10219, M.W. 282.22

Reagents 1.5% (w/v solution in 0.1M sodium acetate buffer pH 5.0) Beta-glucan (Barley;
3,5-Dinitrosalicylic acid (DNS) solution: 10 g DNS, 16 g sodium hydroxide pellets, 300 g potassium sodium (+)-tartrate was dissolved in 1000 ml glass distilled water.
1M Sodium acetate buffer, pH 5.0
Glucose standard solution (1.000 mg/ml)

Procedure

Each enzyme sample assay involves three analyses: duplicate test (TEST) analyses and a blank (BLANK) analysis. A glucose standard curve is also required 0.25 ml diluted enzyme solution was added to 1.75 beta-glucan solution at 50° C., 2 ml DNS solution was added after 10 minutes and the tubes were placed at 95° C. minimum for 15 minutes. Cooled down to 25° C. water.

10 ml of glass distilled water was added and optical density measured at 540 nm (OD$_{540\,nm}$) using a 1 cm path length cuvette.
Determine OD$_{540\,nm}$ TEST for the duplicate TESTS measured;
determine OD$_{540\,nm}$ BLANK;
determine OD$_{540\,nm}$ STANDARDS for 0.125, 0.250, 0.500, 0.750 mg/ml glucose STANDARDS referenced against the 0.00 mg/ml glucose STANDARD sample (or all against water).

Calculation
Determine $\Delta OD_{540\,nm}$ TEST (T)=OD$_{540\,nm}$ TEST−OD$_{540\,nm}$ BLANK The activity is calculated as follows:

$$\text{Activity } (u.ml^{-1} \text{ or } u.g^{-1}) = \frac{T - c}{m} \times A \times \frac{1}{180.16} \times 10^3 \times \frac{1}{V} \times \frac{1}{t} \times D$$

where:

$T = \Delta OD_{540nm}\text{TEST}$ $= OD_{540nm}\text{TEST} - OD_{540nm}\text{BLANK}$ $m$ = gradient of the standard curve (approximately 1.0)

$c$ = y axis intercept of the standard curve
(always negative and approximately −0.02)

180.16 ≡ molecular weight of glucose $10^3$ ≡ to convert to μmoles $A$ ≡ assay volume in ml 2.00 ml used -continued V ≡ enzyme volume in ml 0.25 ml used t ≡ assay time in mintues 10 minutes used D = enzyme dilution factor (e.g. for 1 g diluted to 1 litre D = 1000)

The invention claimed is:

1. An enzyme complex having beta-1,4-endoglucan hydrolase activity comprising:
   a. a fermentation product of *Trichoderma reesei* wherein at least 61 % of the beta-1,4-endoglucan hydrolase activity of the enzyme complex, as measured by the "Assay 1" method, is from the fermentation product of *Trichoderma reesei;* and
   b. one or more enzymes derived from *Penicillium funiculosum* selected from a xylanase (EC 3.2.1.8), a cellulase (EC 3.2.1.4), and a beta-glucanase (EC 3.2.1.6), wherein 30% to 39% of the beta-1,4-endoglucan hydrolase activity of the enzyme complex, as measured by the "Assay 1" method, is from a fermentation product of *Penicillium funiculosum;* wherein the enzyme complex is substantially cell free.

2. The enzyme complex according to claim 1, wherein said one or more enzymes derived from *Penicillium funiculosum* is an expression product obtained by fermentation of said *Penicillium funiculosum*.

3. The enzyme complex according to claim 2, which expression product obtained by fermentation of said *Penicillium funiculosum* comprises a xylanase.

4. The enzyme complex according to claim 1, further comprising one or more enzyme activities selected from the list consisting of endo-1,4-β-xylanase, endo-1,3(4)-β-glucanase, cellulase, laminarinase, endo-1,5-α-L arabinanase, beta-D-glucoside glucohydrolase, β-Xylosidase, cellobiohydrolase, glucan 1,4-beta-glucosidase, xyloglucan-specific exo-beta-1,4-glucanase and α-N Arabinofuranosidase.

5. An enzyme complex having beta-1,4-endoglucan hydrolase activity comprising:
   a. a first expression product obtained by fermentation of *Trichoderma reesei*, wherein the first expression product accounts for at least 61% of the beta-1,4-endoglucan hydrolase activity of the enzyme complex; and
   b. a second expression product obtained by fermentation of *Penicillium funiculosum,* wherein the second expression product accounts for at least 39% of the beta-1,4-endoglucan hydrolase activity of the enzyme complex; wherein the percentages of beta-1,4-endoglucan hydrolase activity are measured by the "Assay 1" method; wherein the enzyme complex is substantially cell free.

6. The enzyme complex according to claim 1, wherein said strain is *Trichoderma reesei* deposited under the Budapest treaty in the American Type Culture Collection (ATCC) having a strain designation GC Cellulose A83 GICC 0004, M03000004 deposited by Danisco A/S on the date of 5 May 2009, or a derivative or progeny thereof.

7. The enzyme complex according to claim 2, wherein said expression product obtained by fermentation of a *Penicillium* fungus is from single culture of the species *Penicillium funiculosum*.

8. The enzyme complex according to claim 7, wherein said strain is *Penicillium funiculosum* deposited under the Budapest treaty in the International Mycological Institute under the number IMI 378536, or a derivative or progeny thereof.

9. The enzyme complex according to claim 1, wherein said expression product obtained by fermentation is from a wild type species.

10. The enzyme complex according to claim 1, having an enzyme activity of at least about 3000 U/g, such as at least about 4000 U/g, such as at least about 5000 U/g, such as at least about 6000 U/g, such as at least about 7000 U/g as measured by "Assay 1" as described herein derived from fermentation of *Trichoderma reesei*.

11. The enzyme complex according to claim 1, having a total enzyme activity of at least about 4000 U/g as measured by "Assay 1"as described herein.

12. The enzyme complex according to claim 1, wherein about 2362 U/g beta-1,4-endoglucan hydrolase activity is from a fermentation product of *Penicillium funiculosum* and wherein about 5315 u/g U/g beta-1,4-endoglucan hydrolase activity is from a fermentation product of *Trichoderma reesei* wherein said units/g (U/g) is determined by "Assay1".

13. The enzyme complex according to claim 1, wherein said enzyme complex contains at least 5 different side activities.

14. The enzyme complex of claim 1 or claim 5 further comprising at least one preservative.

* * * * *